(12) United States Patent
Nagaoka et al.

(10) Patent No.: US 7,452,856 B2
(45) Date of Patent: Nov. 18, 2008

(54) ANTIBACTERIAL PEPTIDE

(75) Inventors: Isao Nagaoka, Bunkyo-ku (JP); Daiju Okuda, Bunkyo-ku (JP); Shin Yomogida, Bunkyo-ku (JP); Hiroshi Tamura, Tokyo (JP)

(73) Assignees: Seikagaku Corporation, Tokyo (JP); Juntendo University, Tokyo (JP)

( * ) Notice: Subject to any disclaimer, the term of this patent is extended or adjusted under 35 U.S.C. 154(b) by 328 days.

(21) Appl. No.: 11/093,875

(22) Filed: Mar. 29, 2005

(65) Prior Publication Data
US 2006/0009374 A1    Jan. 12, 2006

(30) Foreign Application Priority Data
Jul. 6, 2004    (JP)    .............................. 2004-199835

(51) Int. Cl.
*A61K 38/00*    (2006.01)
*C07K 17/00*    (2006.01)

(52) U.S. Cl. .............................. 514/2; 514/12; 514/13; 530/324; 530/326; 530/334

(58) Field of Classification Search ..................... 514/2, 514/12, 13; 530/324, 326, 334
See application file for complete search history.

(56) References Cited

U.S. PATENT DOCUMENTS 6,040,291 A * 3/2000 Hirata .......................... 514/12

FOREIGN PATENT DOCUMENTS

WO    WO 92/01462    2/1992

OTHER PUBLICATIONS

Nagaoka et al. Isolation of cDNA Encoding Guinea Pig Neutrophil Cationic Antibacterial Polypeptide of 11 kDa (CAP11) and Evaluation of CAP11 mRNA Expression during Neutrophil Maturation, Sep. 5, 1997, The Journal of Biological Chemistry, vol. 272, No. 36, pp. 22742-22750.*
Nagaoka et al. Synergistic actions of antibacterial neutrophil defensins and cathelicidins, 2000, Inflamm. Res., vol. 49, pp. 73-79.*
Nagaoka et al. Cathelicidin Family of Antibacterial Peptides CAP18 and CAP11 Inhibit the Exapression of TNF-alpha by Blocking the Binding of LPS to CD14+ Cells, 2001, The Journal of Immunology, vol. 167, pp. 3329-3338.*
Nagaoka et al. Antibacterial cathelicidin pepetide CAP11 inhibits the lipopolysaccahride (LPS)-induced suppression of neutrophil apoptosis by blocking the binding of LPSto target cells, 2004, Inflamm. Res., vol. 53, pp. 609-622.*

Okuda et al. Determination of the Antibacterial and Lipopolysaccharide-Neutralizing Regions of Guinea Pig Neutrophil Cathelicidin Peptide CAP11, Aug. 2006, Antibacterial Agents and Chemotherapy, vol. 50, No. 8, pp. 2602-2607.*
Song Y M et al. entitled "Effects or 1- or d-Pro incorporation into hydrophobic or hydrophilic helix face of amphipathic alpha-helical model peptide on structure and cell selectivity," Biochemical and Biophysical Research Communications, Academic Press Inc., Orlando Florida, US, vol. 314, No. 2, Feb. 6, 2004, pp. 615-621.
Nagaoka Isao et al., entitled "Augmentation of the lipopolysaccharide-neutralizing activities of human cathelicidin CAP18/LL-37-derived antimicrobial peptides by replacemen with hydrophobic and cationic amino acid residues," Clinical and Diagnostic Laboratory Immunology, American Society for Microbiology, US, vol. 9, No. 5, Sep. 2002, pages.
Yomogida Shin et al., entitled "Purification of the 11- and 5-kDa antibacterial polypeptides from guinea pig neutrophils," Archives of Biochemistry and Biophysics, vol. 328 pp. 219-226, Apr. 1996.
Tossi et al., entitled "Identification and characterization of a primary antibacterial domain in CAP18, a lipopolysaccharide binding protein from rabbit leukocytes," FEBS Letters, Elsevier Science Publishers, Amsterdam, NL, vol. 339, No. 1/2, 1994, pp. 108-112.

* cited by examiner

*Primary Examiner*—Jon P Weber
*Assistant Examiner*—Abdel A Mohamed
(74) *Attorney, Agent, or Firm*—Factor & Lake, Ltd.

(57) ABSTRACT

The present invention provides a novel peptide based on CAP11 as well as provides an antibacterial agent, an LPS-cell-binding inhibitor, and a drug such as a bacterial-infection-treating agent or an endotoxin-shock suppressant, each containing the peptide as an active ingredient. The peptide has the following amino acid sequence (SEQ ID NO: 1): X01 X02 X03 X03 X04 X02 X03 X03 X05 X04 X03 X04 X02 X01 X03 X02 X05 X03 (wherein X01 represents a cationic amino acid residue or a polar uncharged amino acid residue, X02 represents a non-polar amino acid residue, X03 represents a cationic amino acid residue, X04 represents a non-polar amino acid residue or a cationic amino acid residue, and X05 represents a non-polar amino acid residue or a polar uncharged amino acid residue). Each of the antibacterial agent, lipopolysaccharide-cell-binding inhibitor, and drug (e.g., bacterial-infection-treating agent or endotoxin-shock suppressant) contains the peptide as an active ingredient. The present invention also provides for a peptide comprised of a sequence of cationic and non-polar or polar uncharged amino acids forming an α-helix wherein the amino acids are arranged along the α-helix such that when represented as a helical wheel, there is a substantial bi-lateral symmetry between cationic versus non-polar or polar uncharged amino acids.

6 Claims, 6 Drawing Sheets

Fig. 1

Guinia pig CAP11
```
                1                                              43
                GLRKKFRKTRKRIQKLGRKIGKTGRKVWKAWREYGQIPYPCRI
                                                            |
                GLRKKFRKTRKRIQKLGRKIGKTGRKVWKAWREYGQIPYPCRI
```

*CAP11(1-33)*
GLRKKFRKTRKRIQKLGRKIGKTGRKVWKAWRE

*CAP11(1-18)*                          *CAP11(34-43)*
GLRKKFRKTRKRIQKLGR                     YGQIPYPCRI

*CAP11(16-33)*
LGRKIGKTGRKVWKAWRE

*CAP11(9-26)*
TRKRIQKLGRKIGKTGR

Fig. 3

| | |
|---|---|
| CAP11 | GLRKKFRKTRKRIQKLGRKIGKTGRKVWKAWREYGQIPYPCRI |
| 1-18 | GLRKKFRKTRKRIQKLGR |
| 1-18m | GLRKLFRKLLKLIQKLLR |
| 1-18m2 | KLRKLFRKLLKLIRKLLR |

ANTIBACTERIAL PEPTIDE

RELATED APPLICATIONS

This application claims the benefit of the filing date of Japanese Application No. 2004-199835 filed on Jul. 6, 2004, of which the contents of such documents are incorporated herein by reference.

BACKGROUND OF THE INVENTION

1. Field of the Invention

The present invention relates to antibacterial peptides and, more particularly, to antibacterial peptides which are partial peptide based upon the amino acid sequences of a guinea-pig-derived antimicrobial polypeptide and partially substituted forms of this peptide. The present invention also relates to antimicrobial agents; to inhibitors for inhibiting binding of lipopolysaccharide to a cell (hereinafter referred to as lipopolysaccharide-cell-binding inhibitor); and to a drugs such as a bacterial-infection-treating agents or endotoxin-shock suppressants, each employing the antibacterial peptides as an active ingredient.

2. Background Art

In the present specification, the following abbreviations are used.

CAP 11: cationic antibacterial polypeptide of 11 kDa
*E. coli*: *Escherichia coli*
FCS: fetal calf serum
HPLC: high performance liquid chromatography
LPS: lipopolysaccharide, also called endotoxin
MRSA: methicillin-resistant *Staphylococcus aureus*
MSSA: methicillin-sensitive *Staphylococcus aureus*
PBS: phosphate-buffered physiological saline
*S. aur*: *Staphylococcus aureus*
SDS-PAGE: sodium dodecyl sulfate-polyacrylamide gel electrophoresis CAP11 is an antibacterial polypeptide found in guinea-pig neutrophils and is known to be a homodimer consisting of peptides that are linked via a cysteine disulfide bond (S—S bond) with each peptide having 43 amino acid units (Yomogida, S., et al., Archives of Biochemistry and Biophysics, Vol. 328, p. 219-226 (1996)). CAP11 is known to exhibit a potent antibacterial effect to gram-positive and gram-negative bacteria and is known to neutralize bioactivity of gram-negative bacteria LPS (Nagaoka, I. et al., Inflammation Research, Vol. 49, p. 73-79 (2000) and Nagaoka, I. et al., Journal of Immunology, Vol. 167, p. 3329-3338 (2001)).

U.S. Pat. No. 6,040,291 issued to Hirata (hereafter "Hirata '291") discloses a partial peptide of CAP18 (cationic antibacterial polypeptide of 18 kDa) having antimicrobial and LPS-binding activities.

If the aforementioned effects of CAP18 or CAP 11 are obtained from a peptide of smaller size, and if its activity is higher than known partial peptide of CAP18 or CAP 11, antibacterial agents and various drugs showing strong activities could be produced more speedily and easily at a lower cost, while facilitating quality control of the products and other operations. Also, if such partial peptides exceed the efficacy of CAP 11 or the partial peptides of CAP 18, the benefits would be even greater.

Hirata '291 discloses enhancements to partial peptides of CAP 18 by substituting certain amino acids naturally occurring in the CAP 11 partial peptide sequence so as to effect a different balance between hydrophobic and hydrophilic amino acids. Hirata '291 proposed that the reason why the peptides of its disclosure have high antimicrobial activity, the high endotoxin (LPS)-binding activity and the high endotoxin (LPS)-neutralizing activity is that the peptide in the LPS-binding domain of human-derived CAP18 has an alpha-helix structure, which, when projected in its axial direction (depicted as a helical wheel in FIGS. 1 and 3 of Hirata '291) reveals a hydrophilic portion (i.e., a portion which is rich in a hydrophilic amino acid residue (basic amino acid residue) such as arginine and lysine) and a hydrophobic portion (i.e., a portion which is rich in a hydrophobic amino acid residue such as phenylalanine, leucine and isoleucine). Hirata presumed that the hydrophilic portion of the peptide binds ionically to a portion of the phosphate group of the lipid A portion of LPS, and the hydrophobic portion of the peptide hydrophobically binds to the fatty acid portion of the lipid A, resulting in exhibition of the antimicrobial activity and the LPS-neutralizing activity.

Accordingly, Hirata '291 proposed that substitution of specified amino acid residues at specified positions would alter the balance between the hydrophilic portion and the hydrophobic portion (FIGS. 1 and 3) and this change would be associated with an increase in the antimicrobial activity, the LPS-binding activity, and LPS-neutralizing activity.

While Hirata '291 disclosed the concept that designing an amino acid sequence of a partial peptide of CAP 18, by taking into consideration the balance between the hydrophilic portion and the hydrophobic portion in the helical wheel when the alpha-helix structure of the peptide is projected in its axial direction, will increase the antimicrobial activity, the LPS-binding activity, and the LPS-neutralizing activity, it disclosed only substitutions which increased the hydrophobic aspect of the natural partial peptide (of CAP 18) (see FIGS. 2 and 4 of Hirata '297).

In other words, while it appears that the substituted partial peptides according to Hirata '291 are successful to accomplish the stated goals of Hirata '291, the "balance" of the substitutions disclosed in Harata '291 favored a hydrophobic character. Hirata '291 does not disclose making substitutions to a natural peptide amino acid sequence to increase bi-lateral symmetry between the hydrophobic and hydrophilic character of an amino acid sequence of a peptide used as an antimicrobial agent. It follows that Hirata '297 also did not disclose synthesizing a peptide for antimicrobial use having substantial bi-lateral symmetry when viewed axially as a helical wheel, or the enhanced activity of such a peptide.

SUMMARY OF THE INVENTION

The present inventors have carried out extensive studies and have attained the aforementioned effects and have found that: (a) the desired effects are provided from a smaller peptide (CAP 11); (b) a specific partial peptide of CAP11 exhibits a remarkably high antibacterial activity and LPS-cell-binding inhibitory effect; (c) these effects are further enhanced through synthesis of a partial peptide having the structure of CAP 11 except for substitutions of selected amino acid residues of the partial peptide to increase symmetry of the partial peptide such that the amino acids after substitution are arranged along a helix such that when represented in a helical wheel, there is a greater degree of bi-lateral symmetry between the distribution of cationic amino acid residues versus non-polar and/or polar-uncharged amino acids residues than was present in the naturally-occurring partial peptide; and (d) that optimal results are evident in such a peptide when there is substantial bi-lateral symmetry between the population of cationic versus non-polar or polar-uncharged amino acid residues.

One object of the invention is to provide novel peptides according to the above accomplishments. Another object of the invention is to provide an antibacterial agent containing the novel peptides as active ingredients. Still another object of the invention is to provide LPS-cell-binding inhibitors containing the novel peptides as an active ingredient. Yet another object of the invention is to provide drugs such as bacterial-infection-treating agents or endotoxin-shock suppressants, each containing the peptides as an active ingredient.

According to one embodiment of the present invention, there are provided peptides having the following amino acid sequence (hereinafter referred to as "SEQ ID NO: 1"):

X01 X02 X03 X03 X04 X02 X03 X03 X05 X04 X03 X04 X02 X01 X03 X02 X05 X03, wherein X01 represents a cationic amino acid residue or a polar uncharged amino acid residue, X02 represents a non-polar amino acid residue, X03 represents a cationic amino acid residue, X04 represents a non-polar amino acid residue or a cationic amino acid residue, and X05 represents a non-polar amino acid residue or a polar uncharged amino acid residue.

According to another embodiment of the invention the cationic amino acids in SEQ ID NO: 1 are Lys or Arg, the polar uncharged amino acid is Thr, Gly, or Gln, and the non-polar amino acid is Leu, Ile, or Phe. Preferably, X04 and X05 are both non-polar amino acid residues.

Another partial peptide embodiment according to the present invention has the following amino acid sequence (hereinafter "SEQ ID NO: 2:"):

X06 Leu Arg Lys X07 Phe Arg Lys X08 X09 Lys X09 Ile X10 Lys Leu X11 Arg, wherein X06 represents Gly or Lys, X07 represents Lys or Leu, X08 represents Thr or Leu, X09 represents Arg or Leu, X10 represents Gln or Arg, and X11 represents Gly or Leu.

According to another embodiment of the present invention, a peptide has any of the amino acid sequences of (a) to (c):

(a) Gly Leu Arg Lys Lys Phe Arg Lys Thr Arg Lys Arg Ile Gln Lys Leu Gly Arg (hereinafter, "SEQ ID NO: 3");

(b) Gly Leu Arg Lys Leu Phe Arg Lys Leu Leu Lys Leu Ile Gln Lys Leu Leu Arg (hereinafter, "SEQ ID NO: 4"); and (c) Lys Leu Arg Lys Leu Phe Arg Lys Leu Leu Lys Leu Ile Arg Lys Leu Leu Arg (hereinafter, "SEQ ID NO: 5").

It is noted that SEQ ID NO: 3 is represented in FIG. 2A, while SEQ ID NOS: 4 and 5 are represented in FIGS. 2B and 2C respectively.

According to another embodiment of the present invention, there is provided an antibacterial agent comprising any one of the peptides of the present invention as an active ingredient (hereinafter referred to as "the antibacterial agents of the present invention").

According to another embodiment of the present invention, there is provided an LPS-cell-binding inhibitor comprising any one of the peptides of the present invention as an active ingredient (hereinafter referred to as "the inhibitors of the present invention").

According to another embodiment of the present invention, there is provided a drug comprising any one of the peptides of the present invention as an active ingredient (hereinafter referred to as "the drugs of the present invention"). The drugs provided according to present invention include bacterial-infection-treating agents and endotoxin-shock suppressants.

Preferred peptides of the present invention are specific partial peptides of a guinea-pig-derived antibacterial polypeptide (CAP11) or a synthesized peptide produced where certain amino acid residues at specific positions of the partial peptide are substituted from the amino acids occurring in the naturally-occurring peptide. The peptides of the invention are very useful, since the peptides are endowed with high antibacterial activity and LPS-cell-binding inhibitory effect. In addition, the peptides of the present invention are remarkably beneficial, since the peptides are much smaller and can be produced more speedily and easily at lower cost, while facilitating quality control of the products and other operations.

Since the peptides of the present invention exhibit high pharmacological effect, the amount of the active ingredient (i.e., the peptides of the present invention) contained in the antibacterial agents of the present invention, the inhibitors of the present invention, or the drugs of the present invention can be reduced, whereby such products can be provided with higher safety at lower cost. Thus, the peptides of the present invention are of high utility.

BRIEF DESCRIPTION OF THE DRAWINGS

Various other objects, features, and many of the attendant advantages of the present invention will be readily appreciated as the same becomes better understood with reference to the following detailed description of preferred embodiments when considered in connection with the accompanying drawings, in which:

FIG. 1 shows the amino acid sequence of CAP11 (SEQ ID NO: 6) and amino acid sequences of CAP11, 1-33, 1-18 (SEQ ID NO: 3), 34-43, 16-33 (SEQ ID NO: 7), and 9-26 (SEQ ID NO: 8);

FIG. 3 shows amino acid sequences of peptides CAP11 (SEQ ID NO: 6), a partial peptide of CAP11 (1-18) (SEQ ID NO: 3) and two synthesized and substituted peptides 1-18m (SEQ ID NO: 4) and 1-18m2 (SEQ ID NO: 5) according to the present invention;

DETAILED DESCRIPTION OF PREFERRED EMBODIMENTS

Preferred embodiments of the present invention will next be described in detail with reference to the attached drawings.

<1> The Peptides of the Present Invention

According to one aspect of the invention it is proposed that a partial peptide of CAP 11 be employed as an antimicrobial agent; a lipopolysaccharide-cell-binding inhibitor; and, a drug such as a bacterial-infection-treating agent or an endotoxin-shock suppressant. FIG. 1 discloses the amino acid sequences of CAP 11 and partial peptides thereof, including the partial peptide 1-18.

Figure 2A:
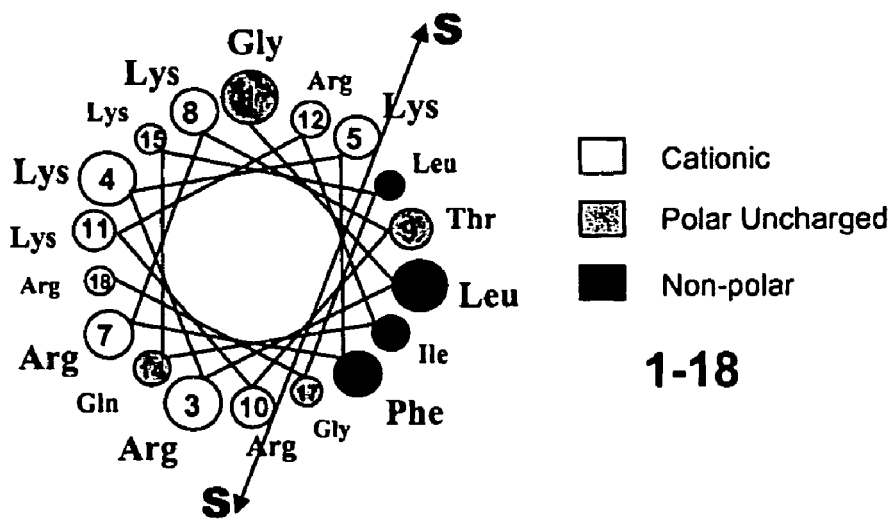
FIG. 2A shows a helical wheel representation of a partial peptide 1-18 of CAP11 (SEQ ID NO: 3) according to the present invention.
Figure 2B:
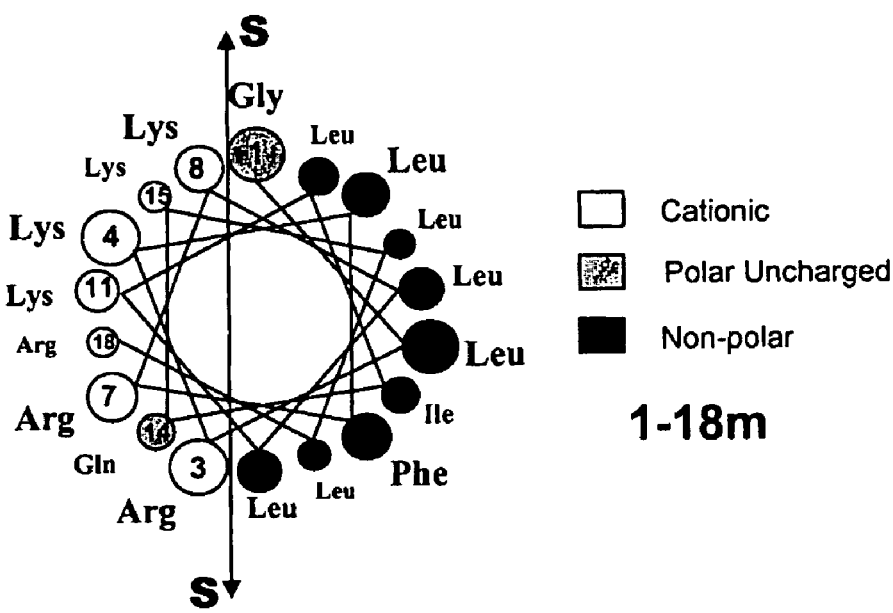
FIG. 2B shows a helical wheel representation of a peptide 1-18m (SEQ ID NO: 4) according to the present invention which is a synthesized and substituted form of 1-18 (SEQ ID NO: 3) shown in FIG. 2A.
Figure 2C:
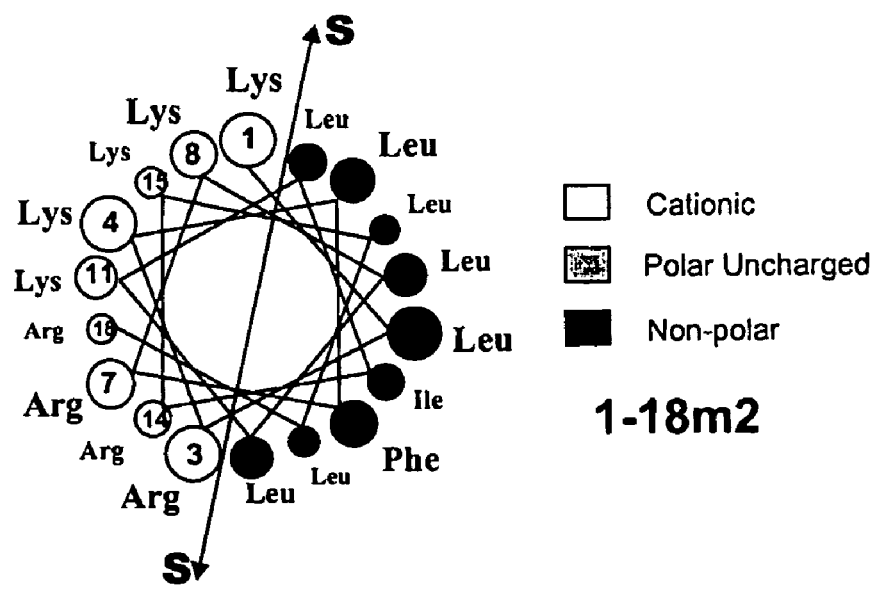
FIG. 2C shows a helical wheel representation of a peptide 1-18m2 (SEQ ID NO: 5) according to the present invention, which is a synthesized and substituted form of 1-18 (SEQ ID NO: 3) shown in FIG. 2A.

CAP11 has an α-helix structure. FIG. 2A shows a helical wheel representation (i.e. a projection of an α-helix structure in its axial direction) of the amino acid sequence (from the 1st amino acid to the 18th amino acid from the N-terminus) of the partial peptide 1-18 of CAP11 (i.e., the aforementioned and below identified peptide SEQ ID NO: 3). In FIG. 2, black dots denote non-polar amino acids, gray dots denote polar uncharged amino acids, and white dots denote cationic amino acids. As can be seen in the helical wheel representation, a portion on one side of a co-axial lateral division of the helix (indicated by arrows S—S of FIGS. 2A-2C) is relatively rich in cationic amino acid residues and a portion on the other side of the lateral division (arrows S—S of FIGS. 2A-2C) is comparatively rich in non-polar amino acid residue.

Peptides according to this aspect as well as more preferred aspects of the of the invention have the following amino acid sequence (SEQ ID NO: 1):

X01 X02 X03 X03 X04 X02 X03 X03 X05 X04 X03 X04 X02 X01 X03 X02 X05 X03, where X01 represents a cationic amino acid residue or a polar uncharged amino acid residue, X02 represents a non-polar amino acid residue, X03 represents a cationic amino acid residue, X04 represents a non-polar amino acid residue or a cationic amino acid residue, and X05 represents a non-polar amino acid residue or a polar uncharged amino acid residue.

The "cationic amino acid" may include Lys (lysine), Arg (arginine), and His (histidine). The "polar uncharged amino acid" includes Gly (glycine), Gln (glutamine), Asn (asparagine), Ser (serine), Thr (threonine), and Tyr (tyrosine). The "non-polar amino acid" may include Leu (leucine), Ile (isoleucine), Phe (phenylalanine), Ala (alanine), Val (valine), Pro (proline), Met (methionine), Trp (tryptophan), and Cys (cysteine).

Among them, the cationic amino acid is preferably Lys or Arg, the polar uncharged amino acid is preferably Thr, Gly, or Gln, and the non-polar amino acid is preferably Leu, Ile, or Phe.

Preferably, each of X04 and X05 is a non-polar amino acid residue.

Peptides represented by the amino acid sequence of SEQ ID NO: 1, contain residues X01 to X05, each with a plurality of occurrences. Amino acid residues represented by each of X01 to X05 are not necessarily identical to one another. For example, X01 located at the first position as counted from the N-terminus and XO1 located at the 14th position as counted from the N-terminus) may be identical to or different from each other. The same is applied to X02 to X05.

More preferably, the peptides of the present invention have the following amino acid sequence of SEQ ID NO: 2:

X06 Leu Arg Lys X07 Phe Arg Lys X08×09 Lys X09 Ile X10 Lys Leu X11 Arg, wherein X06 represents Gly or Lys, X07 represents Lys or Leu, X08 represents Thr or Leu, X09 represents Arg or Leu, X10 represents Gln or Arg, and X11 represents Gly or Leu.

The peptides of the present invention represented by the amino acid sequence of SEQ ID NO: 2 contain a plurality of X09. Similar to the above case, amino acids represented by X09 are not necessarily identical to one another. For example, one of X09 which is at the 10th position and X09 which is at the 12th position may be Arg, and the other may be Leu.

Most preferably, peptides of the present invention have any one of the amino acid sequences of (a) to (c):

(a) Gly Leu Arg Lys Lys Phe Arg Lys Thr Arg Lys Arg Ile Gln Lys Leu Gly Arg (SEQ ID NO: 3);

(b) Gly Leu Arg Lys Leu Phe Arg Lys Leu Leu Lys Leu Ile Gln Lys Leu Leu Arg (SEQ ID NO: 4); and (c) Lys Leu Arg Lys Leu Phe Arg Lys Leu Leu Lys Leu Ile Arg Lys Leu Leu Arg (SEQ ID NO: 5).

Among them, the peptides having the sequence (b) and those having the sequence (c) are preferred, with the peptide having the sequence (c) being particularly preferred. Hereinafter, peptides having any of the sequences (a) to (c) may be referred to as the peptide (a), (b), or (c) of the present invention.

Notably, the peptide according to SEQ ID NO: 3 is the naturally-occurring partial peptide of CAP 11 (1-18) while the peptides according to SEQ ID NOS: 4 and 5 embody an additional aspect of the invention. In particular, as disclosed in FIG. 2B peptides according to SEQ ID NO: 4 are synthesized to deviate from the naturally-occurring partial peptide amino acid sequence so as to provide a greater degree of bi-lateral symmetry between cationic and polar uncharged or non-polar amino acids. As disclosed in FIGS. 6 and 7 the peptide 1-18m (FIG. 2B) shows improved performance over the partial peptide 1-18 of CAP 11.

Figure 6:
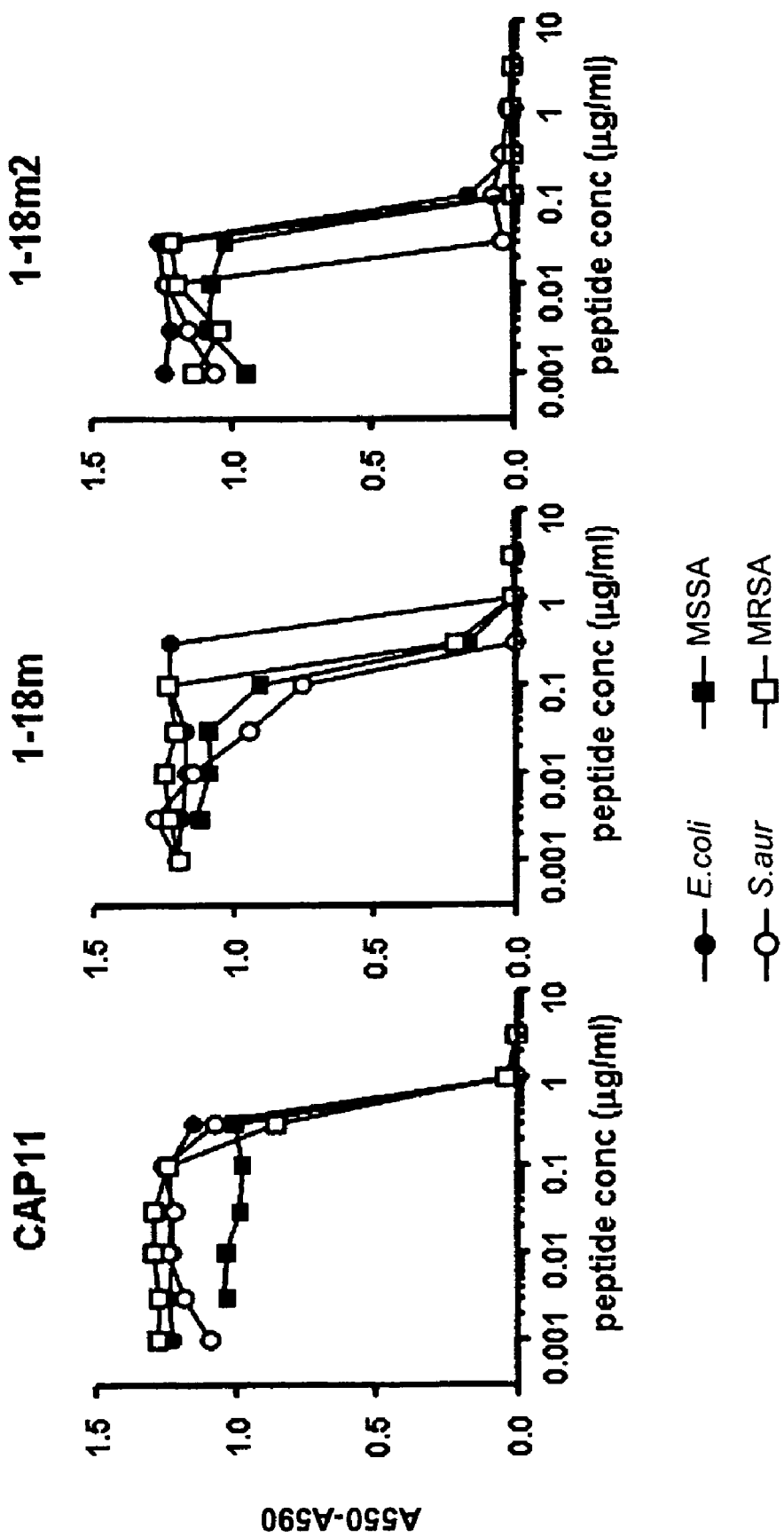
FIG. 6 is three graphs showing antibacterial effects of the partial peptide 1-18 of CAP 11, and two synthesized peptides 1-18m, and 1-18m2.
Figure 7:
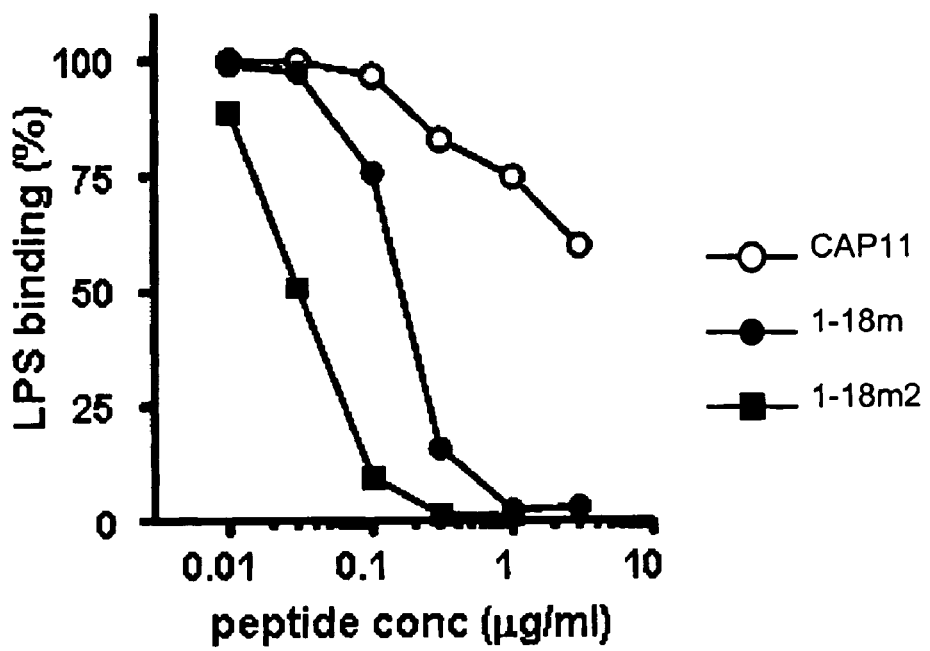
FIG. 7 is a graph showing LPS-binding inhibitory effects peptide1-18 of CAP 11, and synthesized peptides 1-18m, and 1-18m2; and, FIG. 8 is a graph showing antibacterial (antifungal) effects of CAP 11 monomer, and synthesized and substituted peptides 1-18m, and 1-18m2.

FIG. 2C discloses another preferred embodiment of a synthesized and substituted peptide 1-18m2 according to SEQ ID NO: 5, wherein there is substantial, if not complete, bilateral symmetry between cationic amino acids versus non-polar or polar uncharged amino acids arranged throughout its helix. FIGS. 6 and 7 disclose that this embodiment is superior to both peptides according to SEQ ID NOS: 3 and 4.

As noted above, the peptides of the present invention have amino acid sequences designed in consideration of the balance between the cationic moieties and the non-polar or uncharged moieties observed in a helical wheel representation, which is a projection of an α-helix structure in its axial direction. FIGS. 6 and 7 as well as the examples disclosed below, indicate that the antibacterial effect and the LPS-cell-binding inhibitory effect of the peptides can be successfully enhanced. The peptides of the present invention also encompass peptides containing the cationic moieties and the non-polar or polar uncharged moieties at such balanced ratios as shown in the helical wheel in FIG. 2A-2C.

According to one aspect of the invention, a peptide comprised of a sequence of cationic and non-polar or polar uncharged amino acids forming an α-helix wherein the amino acids are arranged along the α-helix such that when represented as a helical wheel, there is an enhanced and substantial bi-lateral symmetry between the cationic versus the non-polar or polar uncharged amino acids. Considering the performance of the peptides comprised by SEQ ID NOS: 3-5, and the disclosure of Hirata '291, it would appear that a reasonable measure for a degree of significant performance or enhanced performance for a substituted peptide is the degree of bilateral symmetry which can be visually identified by the helical wheels of FIGS. 2A-2C and the arrows S—S. However, a degree of symmetry can be calculated by counting the number of moieties on each side of the arrows S—S which forms the line of bilateral symmetry. A percentage can then be considered e.g. FIG. 2C and SEQ ID NO: 5 disclose that there are 9 cationic amino acids on one side, and 9 non-polar or polar uncharged amino acids on the other side of the arrow S—S giving a ratio of 50/50 or 50%. The peptide of SEQ ID NO: 4, on the other hand, has 8 cationic amino acids on one side of the bilateral arrow S—S (FIG. 2B) while having 10 non-polar or polar uncharged amino acids on the other side of the bilateral line. This provides a ratio of 8 over a total of 18 amino acids or a percentage of 44.4% and a ratio range of 44.4% to 55.6%. While this ratio provides better results than that of the CAP 11 (1-18) partial peptide, it is not as substantial as the fully symmetrical 1-18m2 amino acid sequence.

Other examples of such peptides include peptides having amino acid sequences which are the reverse of that of the corresponding amino acid sequence identified above, and peptides containing D-amino acids corresponding to the L form, and peptides containing an amino acid generally not found in protein (e.g., β-alanine, γ-aminobutyric acid, homocysteine, ornithine, 5-hydroxytryptophane, 3,4-dihydroxyphenylalanine, triiodothyronine, or thyroxine). Among them, most preferred are amino acid sequences disclosed in the present specification which are composed of L-amino acids generally found in protein.

Also, the peptides of the present invention include those peptides obtained by modifying the peptides of the present invention. Examples of such peptides include peptides whose α-amino group or α-carboxyl group is modified and peptides which have modified side chain functional groups.

<2> Synthesis of Peptides

The peptide of the present invention can be produced by a chemical peptide synthesis method known per se (through, for example, liquid phase synthesis or solid phase synthesis; see IZUMIYA Nobuo, KATO Tetsuo, AOYAGI Haruhiko, and WAKI Michinori, "Fundamentals and Experiments of Peptide Synthesis", 1985, Maruzen Co., Ltd.) based on the concepts disclosed herein. For example, to produce a peptide having the amino acid sequence shown in SEQ ID NO: 1 through solid phase synthesis, if the 18-position in the amino acid sequence is Arg, then the peptide having the amino acid sequence shown in SEQ ID NO: 1 can be obtained by binding the carboxyl group of an α-amino group (Nα)-protected-arginine to an insoluble resin having a chloromethyl group or an oxymethyl group directly or through a spacer, removing the Nα-protecting group, sequentially binding each protected amino acid (an amino acid protected by Nα or by a side-chain functional group, if any, is referred to simply as protected amino acid) in the 17-position to 1-position of the amino acid sequence through solid phase synthesis, and then eliminating the insoluble resin and the protecting group in the (Nα)-group or the side chain functional group (if any) of the amino acids.

The above-described insoluble resin having a chloromethyl group or an oxymethyl group, the spacer, or the protected amino acid-bound resin which contains an insoluble resin having a protected amino acid bound thereto according to needs, used for synthesis of the peptide of the present invention, can be prepared by known conventional methods. Alternatively, suitable ones may be available from among various commercial products.

As the insoluble resin, any resin may be employed so long as it can bind to the carboxyl group of the protected amino acid on the C-terminus directly or, if necessary, through a spacer, and thereafter can be eliminated. Preferred insoluble resins are, for example, chloromethyl resin (chloromethylated styrene/divinylbenzene copolymer), an oxymethyl resin, or 4-oxymethyl-Pam (phenylacetamide methyl)-resin having a spacer introduced therein in the case of a Boc (t-butyloxycarbonyl) strategy, or an oxymethylphenoxymethyl (Wang) resin and derivatives thereof in the case of an Fmoc (9-fluorenylmethyloxycarbonyl) strategy.

The protected amino acid is an amino acid whose functional group or groups is/are protected with a protecting group or groups by a known method, and various protected amino acids are commercially available.

The protecting groups employed in the synthesis of the peptide of the present invention are exemplified below.

First, the protecting group for the α-amino group of an amino acid is Boc (t-butyloxycarbonyl) or Fmoc (9-fluorenylmethyloxycarbonyl). The protecting group for the guanidino group of Arg (arginine) is Tos (tosyl), $NO_2$ (nitro), Mtr (4-methoxy-2,3,6-trimethylbenzenesulfonyl) or Pmc (2,2,5,7,8-pentamethylchroman-6-sulfonyl). The protecting group for the ε-amino group of Lys (lysine) is Z (benzyloxycarbonyl) or Cl.Z (2-cholorobenzyloxycarbonyl), Boc, or Npys (3-nitro-2-pyridinesulfenyl). The protecting group for the imidazolyl group of His (histidine) is Tos, Z, Pac (phenacyl), Bom (benzyloxymethyl), Dnp (dinitrophenyl), or Trt (trityl). The protecting group for the mercapto group of Cys (cysteine) may be Bzl (benzyl), MBzl (4-methoxybenzyl), 4-MeBzl (4-methylbenzyl), Acm (acetamidomethyl), Trt, Npys, t-Bu (t-butyl), or t-BuS (t-butylthio). Preferred are MBzl, 4-MeBzl, Trt, Acm, and Npys. The protecting group for the hydroxyl group of Tyr (tyrosine) is Bzl, $Cl_2$.Bzl (2,6-dichlorobenzyl), or t-Bu or the hydroxyl group of Tyr may be non-protected. The protecting group for the indole group of Trp (tryptophan) is CHO (formyl), or the indole group of Trp may be non-protected. The protecting group for the thiomethyl group of Met (methionine) is methyl sulfoxide, or the thiomethyl group of Met may be non-protected. The protecting group for the hydroxyl group of Ser (serine) and Thr (threonine) is Bzl or t-Bu. The protecting group for the carbamide group of Asn (asparagine) and Gln (glutamine) is Trt or Xan (xanthyl).

Each protective group is preferably selected appropriately from among those conventionally known per se in accordance with the conditions of peptide synthesis.

Binding of the protected amino acid is achieved through a known condensation method such as the DCC (dicyclohexylcarbodiimide) method, DIPCDI (diisopropylcarbodiimide) method (Tartar, A., et al.; J. Org. Chem., 44, 5000 (1979)), activated ester method, mixed or symmetric acid anhydride method, carbonyldiimidazole method, DCC-HONSu (N-hydroxysuccinimide) method (Weygand, F., et al., Z. Naturforsch., B, 21, 426 (1966)), DCC-HOBt (1-hydroxybenzotriazole) method (Koenig, W., et al.; Chem. Ber., 103, 788, 2024, 2034 (1970)), diphenylphosphorylazide method, a BOP-HOBt method (Hudson, D., J. Org. Chem., 53, 617 (1988)) using a BOP reagent (benzotriazolyl-N-hydroxytrisdimethylaminophosphonium hexafluorophosphide), the HBTU (2-(1H-benzotriazol-1-yl)-1,1,3,3-tetramethyluronium hexafluorophosphate)-HOBt method (Knorr, R., et al., Tetrahedron Lett., 30, 1927 (1989)), or the TBTU (2-(1H-benzotriazol-1-yl)-1,1,3,3-tetramethyluronium tetrafluoroborate)-HOBt method (Knorr, R., et al., Tetrahedron Lett., 30, 1927 (1989)).

The condensation reaction is usually carried out in an organic solvent such as dichloromethane, dimethylformamide (DMF), or N-methylpyrrolidone (NMP) or in a solvent mixture thereof.

As the eliminating reagent for the protective group of α-amino group, there may be used trifluoroacetic acid/dichloromethane, HCl/dioxane, piperidine/DMF, piperidine/NMP, etc., and these are selected appropriately in accordance with the species of the protecting group.

The degree of progress of condensation reaction in each stage of synthesis can be examined by the method of E. Kaiser, et al. [Anal. Biochem., 34, 595 (1970)] (ninhydrin reaction).

As described above, a protected peptide resin having a desired amino acid sequence can be obtained.

Treatment of the protected peptide resin with hydrogen fluoride, TFMSA (trifluoromethanesulfonic acid) [E. Gross ed., Yajima, H., et al.; "The Peptide" 5, 65 (1983), Academic Press], TMSOTf (trimethylsilyl triflate [Fuji, N., et al.; J. Chem. Soc., Chem. Commun., 274 (1987)], TMSBr (trimethylsilylbromide [Fuji, N., et al.; Chem. Pharm. Bull., 35, 3880 (1987)], trifluoroacetic acid, or the like can eliminate the resin and protecting group simultaneously. The above-described eliminating reagent is selected appropriately, taking into consideration the strategy used (Boc or Fmoc) and the identity of the resin and the protecting group. The peptide of the present invention can be produced by a series of the processes described above.

Alternatively, the peptide of the present invention can be produced by producing a polynucleotide (DNA or RNA) which corresponds to the amino acid sequence of the peptide of the present invention and processing the polynucleotide through a genetic engineering technique.

The peptide of the present invention thus produced can be purified by isolation/purification methods for proteins generally known in the field of protein chemistry. Specific examples include extraction, recrystallization, salting out with ammonium sulfate, sodium sulfate, etc., centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, and combinations of these. Most effective is a method by reversed-phase high performance liquid chromatography.

The thus-produced peptide of the present invention can be hydrolyzed with an acid such as hydrochloric acid or methanesulfonic acid, and its amino acid composition can be examined by a known method. This enables verification as to whether or not the peptide of the present invention is produced correctly.

More strictly, the amino acid sequence of the produced peptide is determined by a known amino acid sequencing method (such as the Edman degradation technique) to confirm whether the peptide of the present invention is produced correctly.

The peptides of the present invention encompass salts thereof. As described hereinbelow, the peptide of the present invention is particularly useful as a drug, and hence the salt of the peptide is preferably a pharmaceutically acceptable salt.

The peptide of the present invention may form a salt by addition of an acid. Examples of the acid include inorganic acids (such as hydrochloric acid, hydrobromic acid, phosphoric acid, nitric acid, and sulfuric acid), organic carboxylic acids (such as acetic acid, propionic acid, maleic acid, succinic acid, malic acid, citric acid, tartaric acid, and salicylic acid), acidic sugars such as glucuronic acid, galacturonic acid, gluconic acid, and ascorbic acid, acidic polysaccharides such as hyaluronic acid, chondroitin sulfates, alginic acid, and organic sulfonic acids (such as methanesulfonic acid and p-toluenesulfonic acid). Of these salts, preferred ones are a pharmaceutically acceptable salt.

The peptides of the present invention may form a salt with a basic substance. Examples of the salt include pharmaceutically acceptable salts selected from inorganic base salts such as alkali metal salts (such as sodium salts, lithium salts, and potassium salts), alkaline earth metal salts, and ammonium salts and organic base salts such as diethanolamine salts and cyclohexylamine salts.

As will be apparent from the Examples described hereinbelow, the peptides of the present invention exhibit a strong antibacterial effect and also an LPS-cell-binding inhibitory effect. Therefore, the peptide can be used as an active ingredient of, among other products, an antibacterial agent of the present invention, an inhibitor of the present invention, and a drug of the present invention, as will be described in detail below.

<3> Antibacterial Agents of the Present Invention

The antibacterial agents of the present invention are antibacterial agents which contain the peptides of the present invention as an active ingredient. The antibacterial agents of the present invention have a potent antibacterial effect on various gram-positive bacteria, gram-negative bacteria and fungi.

The antibacterial agents of the present invention essentially contain the peptides of the present invention. For example, the antibacterial agents of the present invention may consist of the peptides of the present invention alone or may be in the form of a composition containing peptide of the present invention and an appropriate carrier.

The antibacterial agent of the present invention may be used as a drug and may be used instead of, or in combination with, a conventional antibacterial agent in such a manner that it is added to foods for the prevention of the foods from bacterial contamination or for preservation.

Also, the antibacterial agents of the present invention may be applied to a surface of a suitable material or mixed with a suitable material to produce an antibacterial material. Such an antibacterial material may be used in various forms such as beads, film, plate, monofilament, unwoven fabric, sponge, cloth, knitted fabric, short fiber, tube, and hollow fiber. Specifically, they can be used as antibacterial composite materials for medical use such as an artificial organ, a catheter, a suture (joining fiber) for surgical operation, a dialysis membrane, and the like as well as sanitary goods, antibacterial filters, and the like.

Among the peptides of the present invention used in the antibacterial agent of the present invention, the peptide having any one of the following amino acid sequences (a) to (c) have a high antibacterial effect as specifically shown in the Examples below and thus are preferred.

(a) Gly Leu Arg Lys Lys Phe Arg Lys Thr Arg Lys Arg Ile Gln Lys Leu Gly Arg (SEQ ID NO: 3);

(b) Gly Leu Arg Lys Leu Phe Arg Lys Leu Leu Lys Leu Ile Gln Lys Leu Leu Arg (SEQ ID NO: 4); and (c) Lys Leu Arg Lys Leu Phe Arg Lys Leu Leu Lys Leu Ile Arg Lys Leu Leu Arg (SEQ ID NO: 5).

Of these, the peptides having the amino acid sequence (b) or (c) is preferred. Particularly, peptides having the amino acid sequence (c) are preferred as an active ingredient.

<4> Inhibitor of the Present Invention

The inhibitors of the present invention are LPS-cell-binding inhibitors which contain the peptides of the present invention as active ingredient. The inhibitors of the present invention strongly inhibit binding of LPS to cells, inter alia, hemocytes (in particular macrophages).

The inhibitors of the present invention essentially contain the peptides of the present invention. For example, the inhibitors of the present invention may consist of the peptides of the present invention alone or may be in the form of a composition containing the peptides of the present invention and an appropriate carrier.

The inhibitors of the present invention can be used not only as a drug, but also as a reagent for experiment or other reagent.

Among the peptides of the present invention used in the inhibitor of the present invention, the peptides having any one of the amino acid sequences (a) to (c) has a high LPS-cell-binding inhibitory effect as specifically shown in the Examples below and thus is preferred.

(a) Gly Leu Arg Lys Lys Phe Arg Lys Thr Arg Lys Arg Ile Gln Lys Leu Gly Arg (SEQ ID NO: 3);
(b) Gly Leu Arg Lys Leu Phe Arg Lys Leu Leu Lys Leu Ile Gln Lys Leu Leu Arg (SEQ ID NO: 4); and
(c) Lys Leu Arg Lys Leu Phe Arg Lys Leu Leu Lys Leu Ile Arg Lys Leu Leu Arg (SEQ ID NO: 5).

Of these, the peptides having the amino acid sequence (b) or (c) is preferred. Particularly, the peptides having the amino acid sequence (c) is preferred as an active ingredient.

<5> Drug of the Present Invention

The drugs of the present invention are drugs which contain the peptides of the present invention as an active ingredient.

The drugs of the present invention can be used for various medical applications based on the effects of the peptides of the present invention such as a high antibacterial effect and a high LPS-cell-binding inhibitory effect as stated above.

The drugs of the present invention may consist of the peptides of the present invention alone or may be in the form of a composition containing the peptides of the present invention and a pharmaceutically acceptable carrier. No particular limitation is imposed on the pharmaceutically acceptable carrier which can be used in the present invention, and there may be employed an excipient, a binder, a lubricant, a colorant, a disintegrant, a buffer, an isotonic agent, a preservative, an anesthetic, or other additives which can be used in the medical field.

The drug of the present invention can be applied through any administration method suitably selected, depending on the purpose of treatment, from injection (subcutaneous, intradermal, intravenous, intraperitoneal, etc.), eye dropping, instillation, percutaneous administration, oral administration, inhalation, and the like.

Also, the dosage form such as injectable preparations (solutions, suspensions, emulsions, solids which are dissolved upon use, etc.), tablets, capsules, granules, powders, liquids, liposome inclusions, ointments, gels, external powders, sprays, inhalation powders, eye drops, eye ointments, suppositories, or pessaries can be selected appropriately depending on the administration method, and the peptides of the present invention can be accordingly formulated.

The dose of the drug of the present invention should be set up individually depending on the purpose of administration e.g. prevention, maintenance, prevention of aggravation, alleviation (improvement of symptom) or cure; the nature of disease; the conditions, sex, and age of patient; the administration method, and the like, and is not limited in a particular way.

Hereafter, representative drugs will be explained.

<5-1> Antibacterial Drug

The antibacterial drugs are drugs which contain the antibacterial agents of the present invention (hereinafter referred to as the antibacterial drugs of the present invention) and contain the peptides of the present invention as an active ingredient.

The antibacterial agents of the present invention, as stated above, have a potent antibacterial effect on gram-positive bacteria, gram-negative bacteria and fungi. Therefore, the antibacterial drugs of the present invention can be applied to various gram-positive bacteria, gram-negative bacteria and fungi. No particular limitation is imposed on the bacteria which are the target of application, but *E. coli* and the like are preferred as the gram-negative bacteria, *S. aur* and the like are preferred as the gram-positive bacteria and *Candida albicans* and the like are preferred as the fungi.

Also, the antibacterial drugs of the present invention can be used on multiple drug resistant gram-positive bacteria (for example, methicillin-resistant *S. aur* (MRSA), methicillin-sensitive *S. aur* (MSSA), vancomycin-resistant enterococci, etc.) and multiple drug resistant gram-negative bacteria (multiple drug resistant *Helicobacter, Shigella, Salmonella*, etc.).

The antibacterial drugs of the present invention exhibit a potent antibacterial effect on *E. coli, S. aur*, particularly methicillin-resistant *S. aur* (MRSA) and methicillin-sensitive *S. aur* (MSSA) and *Candida albicans*, and therefore it is preferred that these bacteria be the target of application.

The antibacterial drugs of the present invention may consist of the peptides of the present invention alone or may be in the form of a composition containing the peptides of the present invention and a pharmaceutically acceptable carrier. No particular limitation is imposed on the pharmaceutically acceptable carrier which can be used, and there may be employed an excipient, a binder, a lubricant, a colorant, a disintegrant, a buffer, an isotonic agent, a preservative, an anesthetic, and the like which can be used in the medical field. Also, it may be used in combination with another antibacterial drug such as lysozyme, antibiotics, and the like.

The antibacterial drugs of the present invention can be used for the treatment of, for example, the part infected with microorganisms outside the body or for the treatment of microbial infection inside the body, and an appropriate administration method can be selected depending on the purpose of treatment, from injection (subcutaneous, intradermal, intravenous, intraperitoneal, etc.), eye dropping, instillation, percutaneous administration, oral administration, inhalation, etc.

Also, the dosage form such as injectable preparations (solutions, suspensions, emulsions, solids which are dissolved upon use, etc.), tablets, capsules, granules, powders, liquids, liposome inclusions, ointments, gels, external powders, sprays, inhalation powders, eye drops, eye ointment, suppositories, pessaries, and the like can be appropriately selected depending on the administration method, and the antibacterial drugs of the present invention can be accordingly formulated.

The dosage of the antibacterial drugs of the present invention should be set up individually depending on the nature of bacteria; the state of infection; the conditions, sex, and age of patient; the administration method; and the like and is not limited particularly. The antibacterial drugs of the present invention may be administered in a dose, per time for an adult, of about 0.003 to 3 mg/kg body weight as the peptides of the present invention.

Among the peptides of the present invention used in the antibacterial drugs of the present invention, the peptides having any one of the following amino acid sequences (a) to (c) have high antibacterial effect as specifically shown in the Examples described below and thus is preferred.

(a) Gly Leu Arg Lys Lys Phe Arg Lys Thr Arg Lys Arg Ile Gln Lys Leu Gly Arg (SEQ ID NO: 3);
(b) Gly Leu Arg Lys Leu Phe Arg Lys Leu Leu Lys Leu Ile Gln Lys Leu Leu Arg (SEQ ID NO: 4); and
(c) Lys Leu Arg Lys Leu Phe Arg Lys Leu Leu Lys Leu Ile Arg Lys Leu Leu Arg (SEQ ID NO: 5).

Of these, the peptides having the amino acid sequence (b) or (c) is preferred, and the peptides having the amino acid sequence (c) are particularly preferred as an active ingredient.

<5-2> Bacterial-Infection-Treating Agent

The bacterial-infection-treating agents of the present invention are bacterial-infection-treating agents which contain the peptides of the present invention as an active ingredient (hereinafter referred to as the bacterial-infection-treating agents of the present invention).

Since the peptides of the present invention serve as the active ingredient of the bacterial-infection-treating agents of the present invention they have a potent antibacterial effect on the gram-positive bacteria, gram-negative bacteria and fungi. The bacterial-infection-treating agents of the present invention can be applied to bacterial infections caused by gram-positive bacteria, gram-negative bacteria and fungi. No particular limitation is imposed on the bacteria which cause the bacterial infections, but bacterial infections caused by *E. coli* and the like are preferred as the gram-negative bacteria-caused infection, bacterial infections caused by *S. aur* and the like are preferred as the gram-positive bacteria-caused infection, and bacterial infections caused by *Candida albicans* and the like are preferred as the fungi-caused infection (fungal infection or mycosis).

Also, the bacterial-infection-treating agents of the present invention can be applied to bacterial infections caused by multiple drug resistant gram-positive bacteria (such as methicillin-resistant *S. aur* (MRSA), methicillin-sensitive *S. aur* (MSSA), and vancomycin-resistant enterococci) and multiple drug resistant gram-negative bacteria (such as multiple drug resistant *Helicobacter, Shigella,* and *Salmonella*).

The bacterial-infection-treating agents of the present invention are preferably applied to bacterial infections caused by *E. coli, S. aur,* especially methicillin-sensitive *S. aur* (MRSA) or methicillin-sensitive *S. aur* (MSSA), or *Candida albicans*.

The bacterial-infection-treating agents of the present invention essentially contain the peptides of the present invention. For example, the bacterial-infection-treating agents of the present invention may consist of the peptides of the present invention alone or may be in the form of a composition containing the peptides of the present invention and a pharmaceutically acceptable carrier. The administration method of the bacterial-infection-treating agents of the present invention can be selected appropriately as in the case of the above-described antibacterial drugs of the present invention, and injection (subcutaneous, intradermal, intravenous, intraperitoneal, etc.) is preferred.

Also, the dosage form of the bacterial-infection-treating agents of the present invention can be selected appropriately depending on the administration method as in the case of the antibacterial drugs of the present invention, and the bacterial-infection-treating agents are preferably formulated into injectable preparations (solutions, suspensions, emulsions, solids which are dissolved upon use, etc.).

The dosage of the bacterial-infection-treating agents of the present invention should be set up individually depending on the nature of bacteria; the state of infection; the conditions, sex, and age of patient; the administration method, and the like, and is not limited particularly. The bacterial-infection-treating agents of the present invention may be administered in a dose, per time for an adult, of about 0.003 to 3 mg/kg body weigh as the peptide of the present invention.

Among the peptides of the present invention used in the bacterial-infection-treating agents of the present invention, the peptides having any one of the following amino acid sequences (a) to (c) have a high antibacterial effect as specifically shown in the Examples described below, and thus is preferred.

(a) Gly Leu Arg Lys Lys Phe Arg Lys Thr Arg Lys Arg Ile Gln Lys Leu Gly Arg (SEQ ID NO: 3);
(b) Gly Leu Arg Lys Leu Phe Arg Lys Leu Leu Lys Leu Ile Gln Lys Leu Leu Arg (SEQ ID NO: 4); and
(c) Lys Leu Arg Lys Leu Phe Arg Lys Leu Leu Lys Leu Ile Arg Lys Leu Leu Arg (SEQ ID NO: 5).

Of these, the peptide having the amino acid sequence (b) or (c) are preferred, and the peptide having the amino acid sequence (c) are particularly preferred as an active ingredient.

<5-3> Endotoxin-Shock Suppressant

The Endotoxin-shock suppressants of the present invention are Endotoxin-shock suppressants which contain the peptides of the present invention as an active ingredient (hereinafter referred to as the suppressants of the present invention).

The Endotoxin-shock suppressants of the present invention have excellent suppressing effect on endotoxin shock involved in sepsis, endotoxin shock involved in gram-negative infections, or the like, and also have an effect of suppressing lethality due to such an endotoxin shock.

The Endotoxin-shock suppressants of the present invention essentially contain the peptides of the present invention. For example, the Endotoxin-shock suppressants of the present invention may consist of the peptides of the present invention alone or may be in the form of a composition containing the peptides of the present invention and a pharmaceutically acceptable carrier. The pharmaceutically acceptable carrier, the administration method, the dosage form, the dose, and the like which can be used are the same as the above-described bacterial-infection-treating agents of the present invention.

The endotoxin-shock suppressants of the present invention preferably contain, as an active ingredient, the peptides having any one of the amino acid sequences (a) to (c).

(a) Gly Leu Arg Lys Lys Phe Arg Lys Thr Arg Lys Arg Ile Gln Lys Leu Gly Arg (SEQ ID NO: 3);
(b) Gly Leu Arg Lys Leu Phe Arg Lys Leu Leu Lys Leu Ile Gln Lys Leu Leu Arg (SEQ ID NO: 4); and
(c) Lys Leu Arg Lys Leu Phe Arg Lys Leu Leu Lys Leu Ile Arg Lys Leu Leu Arg (SEQ ID NO: 5).

Of these, the peptides having the amino acid sequence (b) or (c) are preferred, and the peptides having the amino acid sequence (c) are particularly preferred as an active ingredient.

EXAMPLES

The present invention will next be described in more detail by way of examples.

<1> Preparation of CAP11 and Other Peptides

CAP11 monomer (1-43), represented by the amino acid sequence (SEQ ID NO: 6) (the first line in FIG. 1) and having 43 amino acid units and no cysteine disulfide bond (S—S bond), was produced by Central Laboratory of Medical Science, School of Medicine, Juntendo University, through a solid phase synthesis (Fmoc/PyBop (benzotriazole-1-yl-oxy-tris-pyrrolidino-phosphonium hexafluorophosphate) method. Hereinafter, the monomer is referred to as "monomer" or "1-43 (monomer)."

Intact CAP11 (dimer) was produced by dissolving the momoner in a Tris buffer containing 0.5M guanidine hydrochloride, adding 400 μM oxidized glutathione to the solution, and allowing the mixture to stand at room temperature for 2 to 3 days, thereby inducing dimerization via oxidation. The dimer was subjected to reverse-phase HPLC employing capsule pack C18 column (product of Shiseido Fine Chemicals) and eluted and purified using linear water-acetonitrile gradient. Before use, the molecular weight of the dimer was identified as about 11 kDa, through SDS-PAGE. As shown in the amino acid sequence at the first and second lines in FIG. 1, the CAP11 (dimer) produced through the above procedure is a homodimer consisting of peptides that are linked via an S—S bond, each peptide having 43 amino acid units. Hereinafter, the dimer is referred to as simply "the dimer."

The monomer was treated with 4-vinylpyridine under modification/reduction conditions employing a Tris buffer containing 7M guanidine hydrochloride so as to modify cysteine residues in the monomer, thereby producing a pyridylethylated monomer. Hereinafter, the pyridylethylated monomer is referred to as "Pe-monomer."

A partial peptide represented by the amino acid sequence (SEQ ID NO: 1, 1st to 18th amino acid residues from the N-terminus of the monomer), a partial peptide represented by the amino acid sequence (SEQ ID NO: 7, 16th to 33th amino acid residues), and a partial peptide represented by the amino acid sequence (SEQ ID NO: 8, 9th to 26th amino acid residues) (See FIG. 1) were produced by Central Laboratory of Medical Science, School of Medicine, Juntendo University, through solid phase synthesis (Fmoc/PyBop (benzotriazole-1-yl-oxy-tris-pyrrolidino-phosphonium hexafluorophosphate) method. Hereinafter, these partial peptides are referred to as "1-18" (or "CAP11 (1-18)"), "16-33" (or "CAP11 (16-33)"), and "9-26" (or "CAP11 (9-26)"), respectively. The peptide "1-18" corresponds to the peptide (a) or SEQ ID NO:3 of the present invention.

All the above-produced peptides were obtained in the form of white lyophilized product.

The above-produced peptides were subjected to electrospray ionization (ESI)-mass spectrometry analysis (MS) by use of a Finnigan TSQ700 (product of Thermo Electron Corporation). Each partial peptide was found to have mass values substantially identical with the theoretical values calculated from the amino acid sequence. All the partial peptides were found to have a purity of 97% or higher as calculated from the above mass values.

In each elution pattern of these partial peptides obtained through HPLC (reversed-phase chromatography), a single peak was observed. HPLC was performed under the following conditions:

Column: Cosmosil $C_{18}$ (I.D. 4.6 mm×250 mm) (product of Nacalai Tesque)

Eluent: (A) 0.1% aqueous trifluoroacetic acid solution (B) 70% acetonitrile/0.1% aqueous trifluoroacetic acid solution Concentration gradient; linear gradient of eluent (B) of 10% to 100% (45 minutes)

Flow rate: 1 mL/min

<2> Drug Effect/Pharmacological Test

<2-1> Determination of Antibacterial (Bacteriocidal) Effect

Each of *E. coli, S. aur*, MSSA, and MRSA was subjected to shaking culture overnight at 37° C. by use of a Muller-Hinton medium (product of DIFCO), and the cells precipitated through centrifugation were separated and washed with a Phenol Red-free RPMI 1640 medium. Strains of *E. coli, S. aur*, MSSA, and MRSA were prepared so that the cell concentrations were adjusted to $1\times10^8$ CFU/mL, $2\times10^8$ CFU/mL, $2\times10^8$ CFU/mL, and $2\times10^8$ CFU/mL, respectively, the concentrations being determined from the corresponding absorbance values at 650 nm by means of a spectrophotometer.

By use of a 96-well plate, each cell suspension ($1\times10^6$ CFU/mL) (100 µL), a test substance (10 µL), an RPMI 1640 medium (70 µL), and an Alamar Blue reagent (product of BIOSOURCE) (20 µL) were admixed. In the presence of Alamar Blue, pink fluorescence attributed to live cells is observed, whereas the admixture remains blue when the cells are dead.

Each admixture was incubated at a constant temperature of 37° C. for six hours, and the difference between absorbance at 560 nm and that at 595 nm was obtained.

<2-2> Determination of LPS-Cell-Binding Inhibitory Effect

RAW 246.7 cells (macrophage cell strain) were cultured by use of an RPMI 1640 medium containing 10% FCS and collected. The collected cells were diluted with the same medium so that the cell concentration was adjusted to $5\times10^5$/mL. To the diluted liquid (500 µL), a test substance (5 µL) was added, and the mixture was subjected to shaking culture at 37° C. for 10 minutes. Subsequently, LPS that had been labeled with Alexa 488 (final concentration: 100 ng/mL) was added to the culture, and the mixture was subjected to shaking culture at 37° C. for 15 minutes. The collected cells were washed with PBS (3 mL×2) and suspended again in PBS (300 µL). Binding of Alexa 488-labeled LPS was measured through FACS. Control samples (a sample containing no labeled LPS (background) and an antibacterial-peptide-free sample (maximum LPS binding degree) were treated similarly, and the degree of the inhibitory effect on binding between LPS and RAW 246.7 cells was determined on the basis of comparison with control samples.

Figure 4A:
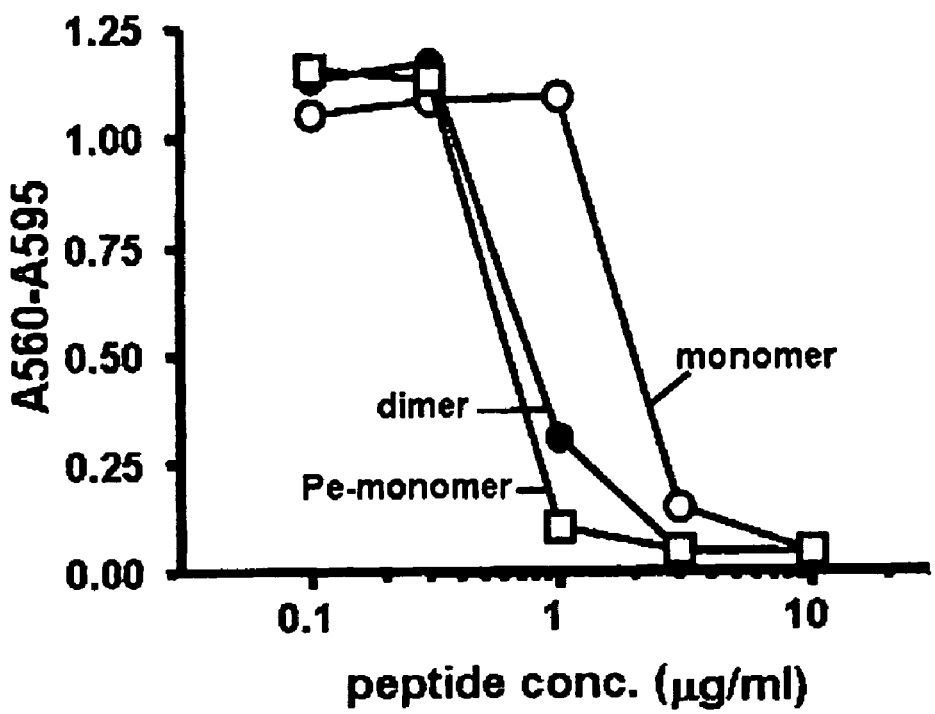
FIG. 4A is a graph showing antibacterial effects of dimer, monomer, and Pe-monomer (Pe: pyridylethylated) forms of CAP 11.
Figure 4B:
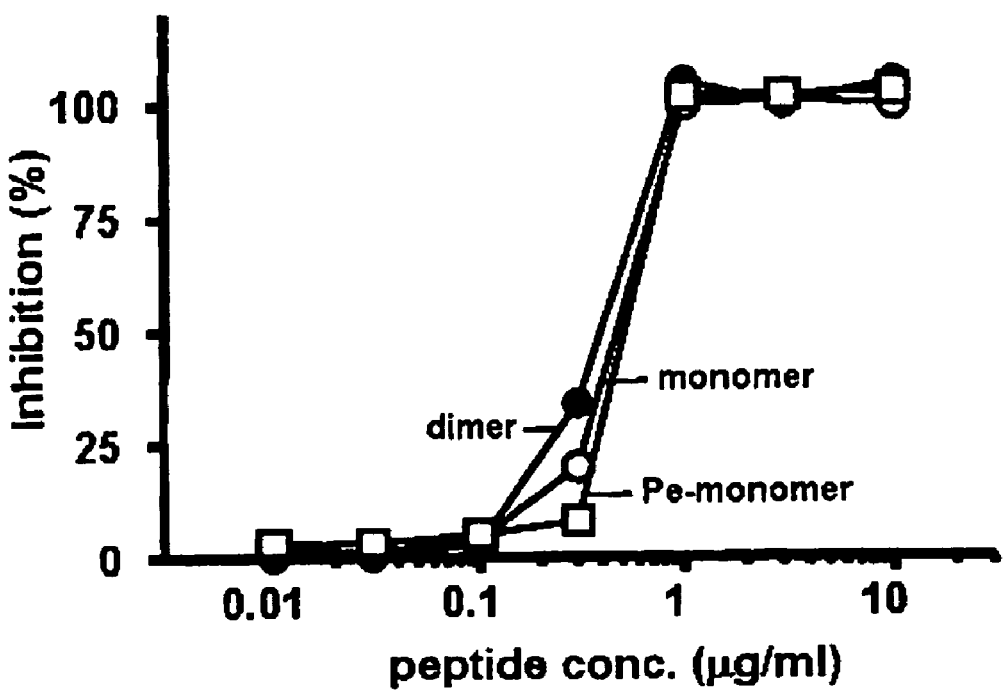
FIG. 4B is a graph showing LPS-binding inhibitory effects of dimer, monomer, and Pe-monomer forms of CAP 11.

FIGS. 4A and 4B show the results when dimer, monomer, and Pe-monomer were tested. FIG. 4A is a graph showing the antibacterial effects (X-axis: test substance concentration, Y-axis: difference between absorbance at 560 nm and that at 595 nm), and FIG. 4B is a graph showing the LPS-cell-binding inhibitory effects (X-axis: test substance concentration, Y-axis: percent inhibition).

As is clear from FIGS. 4A and 4B, all of the dimer, monomer, and Pe-monomer exhibited an antibacterial effect and an LPS-cell-binding inhibitory effect. The antibacterial effect was observed with respect to both gram-negative bacteria and gram-positive bacteria. Dimer and Pe-monomer were found to exhibit a slightly higher antibacterial effect as compared with monomer. No significant difference in LPS-cell-binding inhibitory effect was found among dimer, monomer, and Pe-monomer.

Figure 5A:
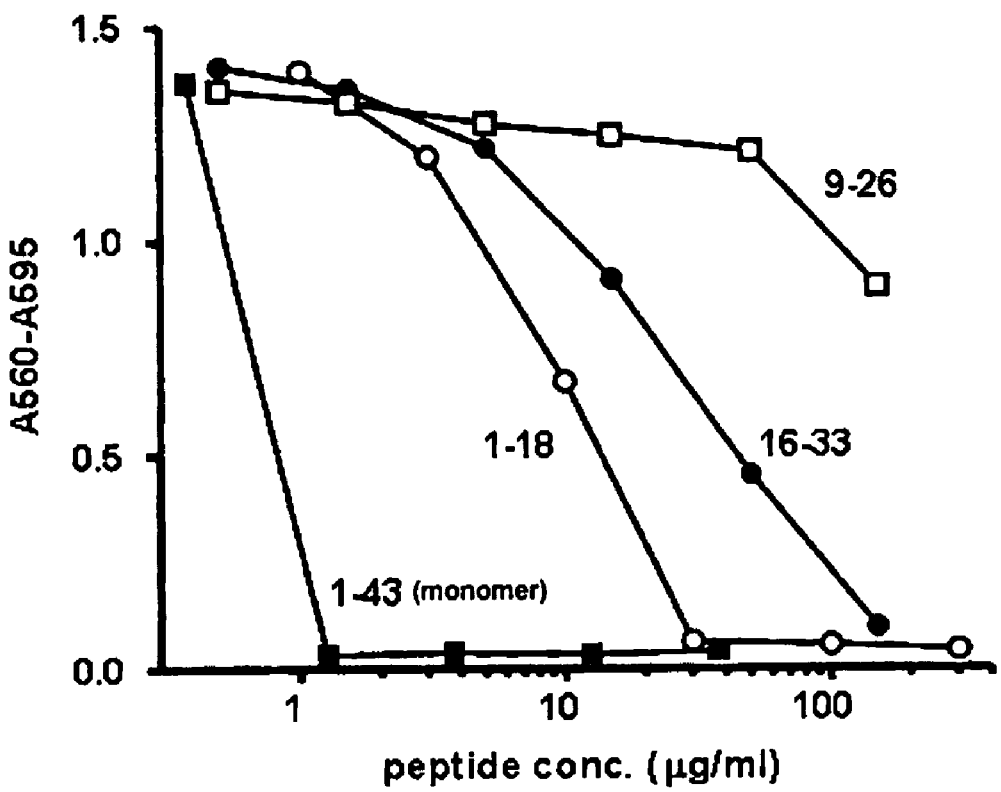
FIG. 5A is a graph showing antibacterial effects of the monomer of CAP 11, and partial peptides of CAP 11, 1-18, 16-33, and 9-26.
Figure 5B:
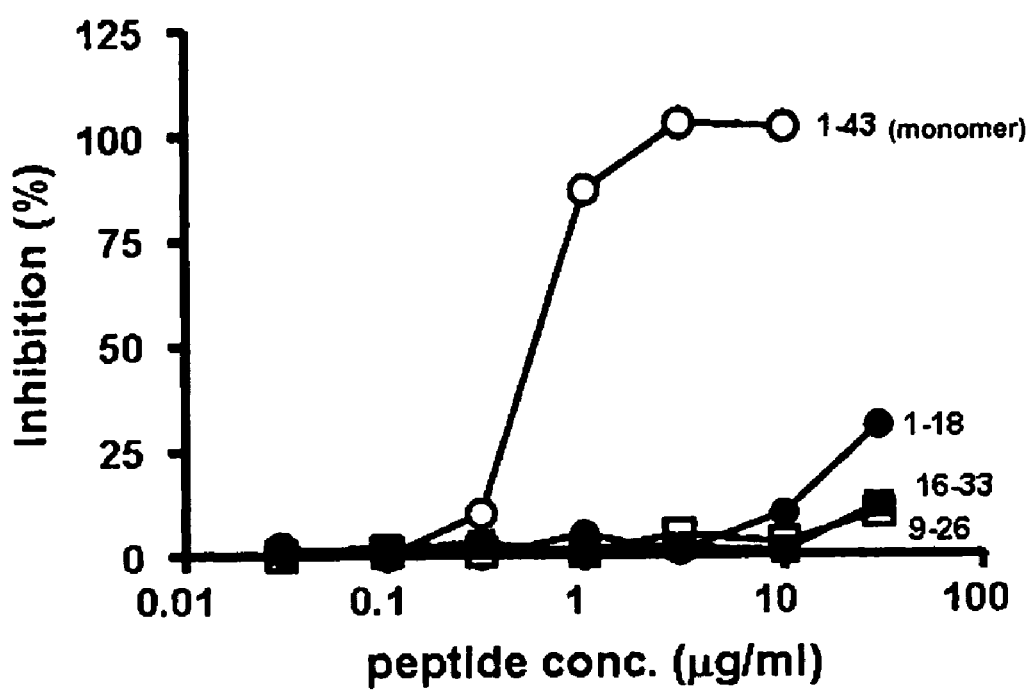
FIG. 5B is a graph showing LPS-binding inhibitory effects of the monomer of CAP 11, and partial peptides of CAP 11, 1-18, 16-33, and 9-26.

FIGS. 5A and 5B show the results when monomer, 1-18, 16-33, and 9-26 tested. FIG. 5A is a graph showing the antibacterial effects (X-axis: test substance concentration, Y-axis: difference between absorbance at 560 nm and that at 595 nm), and FIG. 5B is a graph showing the LPS-cell-binding inhibitory effects (X-axis: test substance concentration, Y-axis: percent inhibition).

As is clear from FIGS. 5A and 5B, all of the monomer, 1-18, 16-33, and 9-26 were exhibited an antibacterial effect and an LPS-cell-binding inhibitory effect. The antibacterial effect was observed with respect to both gram-negative bacteria and gram-positive bacteria. Among partial peptides of the monomer (1-18, 16-33, and 9-26), 1-18 was found to exhibit the most potent antibacterial effect and LPS-cell-binding inhibitory effect.

<3> Preparation of a Peptide (the Peptide According to the Present Invention) from CAP11 (1-18)

FIG. 2 shows a helical wheel representation [1-18] (projection of an α-helix structure its axial direction) of CAP11

(1-18). In FIG. 2, black dots denote non-polar amino acids, gray dots denote polar uncharged amino acids, and white dots denote cationic amino acids.

A portion of the amino acids of CAP11 (1-18) were substituted by other amino acids to thereby prepare modified peptides 1-18m and 1-18m2 shown in FIG. 2. The amino acid sequence of peptide 1-18m and that of peptide 1-18m2 according to the structures shown in FIG. 2 are represented by SEQ ID NOs: 4 and 5, respectively. FIG. 3 also shows these amino acid sequences. In FIG. 3, underlined portions denote substituted amino acids.

The peptide represented by the amino acid sequence (SEQ ID NO: 4) and the peptide represented by the amino acid sequence (SEQ ID NO: 5) were produced by Central Laboratory of Medical Science, School of Medicine, Juntendo University, through solid phase synthesis (Fmoc/PyBop (benzotriazole-1-yl-oxy-tris-pyrrolidino-phosphonium hexafluorophosphate) method. Hereinafter, these peptides are referred to as "1-18m" and "1-18m2," respectively. The peptide "1-18m" corresponds to the peptide (b) of the present invention, and the peptide "1-18m2" corresponds to the peptide (c) of the present invention.

All the above-produced peptides were obtained in the form of white lyophilized product.

The above-produced peptides were subjected to electrospray ionization (ESI)-mass spectrometry analysis (MS) by use of a Finnigan TSQ700 (product of Thermo Electron Corporation). Each peptide was found to have mass values substantially identical with the theoretical values calculated from the amino acid sequence. All the peptides were found to have a purity of 97% or higher as calculated from the above mass values.

In each elution pattern of these peptides obtained through HPLC (reversed-phase chromatography), a single peak was observed. HPLC was performed under the following conditions.

Column: Cosmosil $C_{18}$ (I.D. 4.6 mm×250 mm) (product of Nacalai Tesque)
Eluent: (A) 0.1% aqueous trifluoroacetic acid solution (B) 70% acetonitrile/0.1% aqueous trifluoroacetic acid solution
Concentration gradient; linear gradient of eluent (B) of 10% to 100% (45 minutes)
Flow rate: 1 mL/min <4> Drug Effect/Pharmacological Test <4-1> Determination of Antibacterial (Bacteriocidal) Effect The procedure of the aforementioned <2-1> was repeated, except that 1-18, 1-18m, and 1-18m2 were tested and the difference between absorbance at 550 nm and that at 590 nm was measured, to thereby determine the antibacterial effect of the test substances with respect to each of E. coli, S. aur, MSSA, and MRSA. FIG. 6 shows the test results. In FIG. 6, the test results of 1-18 are represented by "CAP11," and the black dots, white dots, black squares, and white squares denote the antibacterial effects to E. coli, S. aur, MSSA, and MRSA, respectively (X-axis: test substance concentration, Y-axis: difference between absorbance at 550 nm and that at 590 nm).

As is clear from FIG. 6, all of 1-18, 1-18m, and 1-18m2 exhibit an antibacterial (bacteriocidal) effect. The antibacterial effect was observed with respect to both gram-negative bacteria (E. coli) and gram-positive bacteria (S. aur, MSSA, and MRSA). The strongest antibacterial effect is exhibited by 1-18m2, followed by 1-18m and then 1-18.

As mentioned above, U.S. Pat. No. 6,040,291 (Hirata '291) discloses a partial peptide of CAP18 having antimicrobial activity. According to the disclosure of Hirata '291, the strongest antimicrobial activity (IC50) to E. coli, MSSA and MRSA are 0.7 µg/mL, 3.6 µg/mL and 3.2 µg/mL, respectively. FIG. 6 of the present specification shows that the antibacterial activity of the peptide of the present invention is higher than a partial peptide of CAP18.

<4-2> Determination of Antibacterial (Bacteriocidal) Effect (Antifungal Effect) to Fungi Candida albicans (CA53133 strain) was grown in Sabouraud dextrose agar. Colonies formed in the agar were collected and suspended to serum-free and Phenol Red-free RPMI1640 liquid medium (SIGMA). The concentration of cells in the medium was determined from the corresponding absorbance value at 550 nm by means of spectrophotometer, and the concentration is adjusted to $0.5\text{-}2.5\times10^4$ CFU/mL.

By use of a 96-well plate, each cell suspension ($0.5\text{-}2.5\times 10^4$ CFU/mL) (20 µL), a test substance (CAP11, 1-18 or 1-18m2)(10 µL), an RPMI 1640 liquid medium (150 µL), and an Alamar Blue reagent (product of BIOSOURCE) (20 µL) were admixed. Each admixture was incubated at a constant temperature of 35° C. for fourteen hours, and the difference between absorbance at 550 nm and that at 595 nm was obtained.

Figure 8:
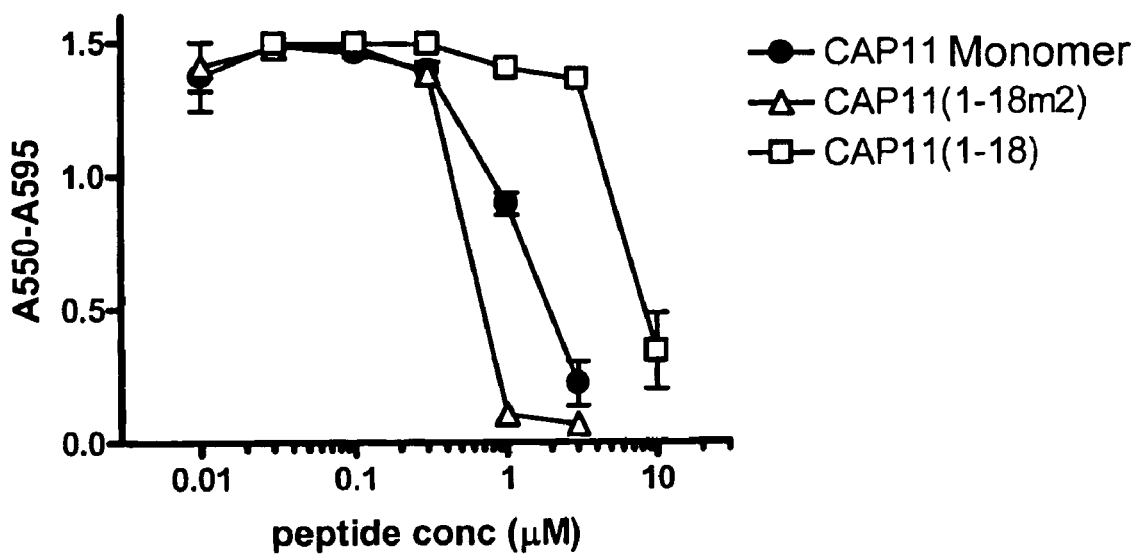

FIG. 8 shows the test results. In FIG. 8, the test results of CAP 11 monomer, 1-18, and 1-18m2 are represented by black circles, white squares, and white triangles, respectively (X-axis: test substance concentration, Y-axis: difference between absorbance at 550 nm and that at 595 nm).

As is clear from FIG. 8, all of CAP1, 1-18, and 1-18m2 exhibit an antibacterial (bacteriocidal) effect to fungi. The strongest antifungal effect is exhibited by 1-18m2.

<4-3> Determination of LPS-Cell-Binding Inhibitory Effect

In a manner similar to that of the aforementioned <2-2>, the LPS-cell-binding inhibitory effect of the same test substances was determined. FIG. 7 shows the test results. In FIG. 7, the test results of 1-18, 1-18m, and 1-18m2 are represented by white dots, black dots, and black squares, respectively (X-axis: test substance concentration, Y-axis: percent binding of LPS to cells).

As is clear from FIG. 7, all of 1-18, 1-18m, and 1-18m2 exhibit an LPS-cell-binding inhibitory effect. The strongest effect is exhibited by 1-18m2, followed by 1-18m and then 1-18.

In septic shock caused by infection with gram-negative bacteria, LPS that is released from cells reacts with monocytes (macrophages), thereby producing a cytokine, nitrogen monoxide (NO), etc., which induce endotoxin shock pathological conditions. When neutrophils are stimulated by LPS, apoptosis of the neutrophils is suppressed, and activated neutrophils cause disorders of tissues involved in septic shock. The aforementioned test results indicate that the peptides of the present invention exhibit a bacteriocidal effect in the case of septic shock, and induces apoptosis of neutrophils by inhibiting binding of LPS to neutrophils. In addition, the peptides of the present invention induce apoptosis of neutrophils by inhibiting binding of LPS to monocytes, thereby inhibiting formation of IL-1β, TNF-α, IL-8, and other cytokines. Furthermore, the peptides of the present invention mitigate endotoxin shock and disorders of tissues involved in gram-negative bacteria infections.

The peptides of the present invention bind to LPS. Through employment of the property, an endotoxin-removing agent containing the peptides of the invention immobilized on a carrier (e.g., an insoluble carrier) may be provided, and other agents may be provided in the same manner.

Formulation Examples

Hereafter, formulation examples of the antibacterial drug of the present invention, the bacterial-infection-treating agent of the present invention, and the suppressant of the present invention will be described. The formulation examples are for illustration only, and the agents of the present invention may take any form.

(1) Antibacterial Drug of the Present Invention (Ointment)

| Peptide of the present invention (c) | 10 mg |
|---|---|
| Sorbitan monostearate | 7 mg |
| Polyoxyethylene sorbitan monostearate | 7 mg |
| Isopropyl palmitate | 37 mg |
| Vaseline | 37 mg |
| Liquid paraffin | 37 mg |
| Cetanol | 50 mg |
| Glycerol | 70 mg |
| Magnesium stearate | 2 mg |

Purified water was added to the above-described components to make 1 g of cream.

(2) Antibacterial Drug of the Present Invention (Tablet)

| Peptide of the present invention (b) | 100 mg |
|---|---|
| Lactose | 670 mg |
| Potato starch | 150 mg |
| Crystalline cellulose | 60 mg |
| Light silicic anhydride | 50 mg |

The above-described components were mixed, and a solution of hydroxypropylcellulose (30 mg) in methanol (10% by weight of hydroxypropylcellulose) was added thereto, followed by kneading and granulating the resultant mixture. The product was extruded through a 0.8 mm-diameter screen, to thereby form granules. After drying, 15 mg of magnesium stearate was added thereto, and the resultant mixture was tabulated in an amount of 200 mg each, to thereby prepare tablets.

(3) Bacterial-Infection-Treating Agent of the Present Invention (Capsule)

| Peptide of the present invention (a) | 100 mg |
|---|---|
| Lactose | 80 mg |

The above-described components were mixed uniformly, and the mixture was charged in hard capsules, to thereby prepare capsule formulation.

(4) Bacterial-Infection-Treating Agent of the Present Invention (Injection)

| Peptide of the present invention (c) | 30 mg |
|---|---|

The above-described component was dissolved in 2 mL of a 5% aqueous mannitol solution, and the solution was filter-sterilized and then sealed in an ampule.

(5) Endotoxin-Shock Suppressant of the Present Invention (Injection Product which is Dissolved upon Use)

(A) Peptide of the present invention (c) (lyophilized) 30 mg (sealed in an ampule)

(B) Filter-sterilized PBS 2 mL (sealed in an ampule)

An injection product which is dissolved upon use containing (A) and (B) was prepared. Upon use, (A) is dissolved in (B).

The peptides of the present invention serve as an active ingredient of the antibacterial agents of the present invention, the inhibitors of the present invention, the drug of the present invention, and other agents and drugs. The antibacterial agents of the present invention serve as an antibacterial agent effective with respect to gram-negative bacteria, gram-positive bacteria and fungi. The inhibitors of the present invention serve as a drug for inhibiting binding of LPS to cells. The drugs of the present invention serve as an antibacterial drug, a bacterial-infection-treating agent, an endotoxin-shock suppressant, and other drugs.

The foregoing description of preferred embodiments is intended only to exemplify principles of the invention and the examples and preferred embodiments are not intended to limit the scope of the claims.

What is claimed is:

1. A peptide, which has the amino acid sequence of Lys Leu Arg Lys Leu Phe Arg Lys Leu Leu Lys Leu Ile Arg Lys Ieu Leu Arg (SEQ ID NO:5).

2. An antibacterial agent comprising a peptide as recited in claim 1 as an active ingredient.

3. A lipopolysaccharide-cell-binding inhibitor comprising a peptide as recited in claim 1 as an active ingredient.

4. A drug comprising a peptide as recited in claim 1 as an active ingredient.

5. A bacterial-infection-treating agent comprising a peptide as recited in claim 1 as an active ingredient.

6. An endotoxin-shock suppressant comprising a peptide as recited in claim 1 as an active ingredient.

* * * * *

SEQUENCE LISTING

```
<160> NUMBER OF SEQ ID NOS: 8

<210> SEQ ID NO 1
<211> LENGTH: 18
<212> TYPE: PRT
<213> ORGANISM: Artificial
<220> FEATURE:
<223> OTHER INFORMATION: A partial peptide of CAP11 wherein Xaa at
      position 1 = basic amino acid or polar uncharged amino acid, Xaa
      at position 2 = nonpolar amino acid, Xaa at position 3 = basic
      amino acid, Xaa at position 4 = basic amino acid, Xaa at position
```

5 = nonpolar amino acid or basic amino acid, Xaa at position 6 = nonpolar amino acid, Xaa at position 7 = basic amino acid, Xaa at p basic amino acid, Xaa at position 9 = nonpolar amino acid or polar uncharged amino acid, Xaa at position 10 = nonpolar amino acid or basic amino acid, Xaa at position 11 = basic amino acid, Xaa at position 12 = nonpolar amino acid or basic amino acid, Xaa at position 13 = nonpolar amino acid, Xaa at position 14 = basic amino acid or polar uncharged amino acid, Xaa at position 15 = basi acid, Xaa at position 16 = nonpolar amino acid, Xaa at position amino acid or polar uncharged amino acid, Xaa at position 18 =

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 2
<211> LENGTH: 18
<212> TYPE: PRT
<213> ORGANISM: Artificial
<220> FEATURE:
<223> OTHER INFORMATION: A partial peptide of CAP11 wherein Xaa at
      position 1 = Gly or Lys, Xaa at position 5 = Lys or Leu, Xaa at
      position 9 = Thr or Leu, Xaa at position 10 = Arg or Leu, Xaa at
      position 12 = Arg or Leu, Xaa at position 14 = Gln or Arg, Xaa at
      position 17 = Gly or Leu.

<400> SEQUENCE: 2

Xaa Leu Arg Lys Xaa Phe Arg Lys Xaa Xaa Lys Xaa Ile Xaa Lys Leu
1               5                   10                  15

Xaa Arg

<210> SEQ ID NO 3
<211> LENGTH: 18
<212> TYPE: PRT
<213> ORGANISM: Artificial
<220> FEATURE:
<223> OTHER INFORMATION: A partial peptide of CAP11

<400> SEQUENCE: 3

Gly Leu Arg Lys Lys Phe Arg Lys Thr Arg Lys Arg Ile Gln Lys Leu
1               5                   10                  15

Gly Arg

<210> SEQ ID NO 4
<211> LENGTH: 18
<212> TYPE: PRT
<213> ORGANISM: Artificial
<220> FEATURE:
<223> OTHER INFORMATION: A partial peptide of CAP11

<400> SEQUENCE: 4

Gly Leu Arg Lys Leu Phe Arg Lys Leu Leu Lys Leu Ile Gln Lys Leu
1               5                   10                  15

Leu Arg

<210> SEQ ID NO 5
<211> LENGTH: 18
<212> TYPE: PRT
<213> ORGANISM: Artificial
<220> FEATURE:
<223> OTHER INFORMATION: A partial peptide of CAP11

<400> SEQUENCE: 5

Lys Leu Arg Lys Leu Phe Arg Lys Leu Leu Lys Leu Ile Arg Lys Leu

```
<210> SEQ ID NO 6
<211> LENGTH: 43
<212> TYPE: PRT
<213> ORGANISM: Artificial
<220> FEATURE:
<223> OTHER INFORMATION: A partial peptide of CAP11

<400> SEQUENCE: 6

Gly Leu Arg Lys Lys Phe Arg Lys Thr Arg Lys Arg Ile Gln Lys Leu
1               5                   10                  15

Gly Arg Lys Ile Gly Lys Thr Gly Arg Lys Val Trp Lys Ala Trp Arg
            20                  25                  30

Glu Tyr Gly Gln Ile Pro Tyr Pro Cys Arg Ile
        35                  40

<210> SEQ ID NO 7
<211> LENGTH: 18
<212> TYPE: PRT
<213> ORGANISM: Artificial
<220> FEATURE:
<223> OTHER INFORMATION: A partial peptide of CAP11

<400> SEQUENCE: 7

Leu Gly Arg Lys Ile Gly Lys Thr Gly Arg Lys Val Trp Lys Ala Trp
1               5                   10                  15

Arg Glu

<210> SEQ ID NO 8
<211> LENGTH: 17
<212> TYPE: PRT
<213> ORGANISM: Artificial
<220> FEATURE:
<223> OTHER INFORMATION: A partial peptide of CAP11

<400> SEQUENCE: 8

Thr Arg Lys Arg Ile Gln Lys Leu Gly Arg Lys Ile Gly Lys Thr Gly
1               5                   10                  15

Arg
```